United States Patent
Eyckerman et al.

(10) Patent No.: US 7,235,629 B2
(45) Date of Patent: Jun. 26, 2007

(54) FUNCTIONAL FRAGMENT OF THE LEPTIN RECEPTOR

(75) Inventors: Sven Eyckerman, Ghent (BE); Jan Tavernier, Balegem (BE); Lennart Zabeau, Ghent (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 360 days.

(21) Appl. No.: 10/415,781

(22) PCT Filed: Oct. 29, 2001

(86) PCT No.: PCT/EP01/12569

§ 371 (c)(1),
(2), (4) Date: Sep. 22, 2003

(87) PCT Pub. No.: WO02/40543

PCT Pub. Date: May 23, 2002

(65) Prior Publication Data

US 2004/0116340 A1      Jun. 17, 2004

Related U.S. Application Data

(60) Provisional application No. 60/248,970, filed on Nov. 15, 2000.

(30) Foreign Application Priority Data

Nov. 14, 2000  (EP) ................................. 00204001

(51) Int. Cl.
*A61K 38/00* (2006.01)
*A61K 38/04* (2006.01)
(52) U.S. Cl. ..................... 530/329; 530/300
(58) Field of Classification Search ............ None
See application file for complete search history.

(56) References Cited

U.S. PATENT DOCUMENTS 5,972,621 A * 10/1999 Tartaglia et al. ............. 435/7.1
6,734,006 B2 * 5/2004 Xiao et al. .................. 435/226

FOREIGN PATENT DOCUMENTS

| WO | WO 97/00319 | | 1/1997 |
|----|----|----|----|
| WO | WO 97/20933 | | 6/1997 |
| WO | WO 97/26335 | * | 7/1997 |
| WO | WO 98/12224 | | 3/1998 |
| WO | WO 99/40946 | A2 | 8/1999 |
| WO | WO 02/40543 | A1 | 5/2002 |
| WO | WO 02/062833 | A2 | 8/2002 |

OTHER PUBLICATIONS

Zabeau et al. 2003 FEBS Letters 546:45-50.*
Bjorbaeki et al. 1999 J Biol Chem 274:30059-30065.*
Bjorbaek et al., The Role of SOCS-3 in Liptin Signaling and Leptin Resistance, The Journal of Biological Chemistry, Oct. 15, 1999, pp. 30059-30065, vol. 274, No. 42.
Mercer et al., Localization of leptin receptor mRNA and the long form splice variant (Ob-Rb) in mouse hypothalamus and adjacent brain regions by in situ hybridization, FEBS Letters, 1996, pp. 113-116, vol. 387.
Tartaglia et al., Identification and Expression Cloning of a Leptin Receptor, OB-R, Cell, Dec. 29, 1995, pp. 1263-1271, vol. 83.
Zabeau et al., The ins and outs of leptin receptor activation, FEBS Letters, 2003, pp. 45-50, vol. 546.
International Preliminary Examination Report, International Application No. PCT/EP01/12569, dated Nov. 5, 2002 (7 pages).
International Search Report, International Application No. PCT/EP01/12569, dated Mar. 28, 2002 (8 pages).
Bonnefoy-Berard, Nathalie, et al., "Vav: Function and Regulation in Hematopoietic Cell Signaling," 14 Stem Cells 250-268 (1996).
Gisselbrecht, Sylvie, "The CIS/SOCS proteins: a family of cytokine-inducible regulators of signaling," 10(4) European Cytokine Network 463-470 (Dec. 1999), retrieved from <URL:http://www.john-libbey-eurotext.fr/articles/ecn/10/4/463-70/> Jul. 12, 2001.
Lee, Gwo-Hwa, et al., "Abnormal splicing of the leptin receptor in diabetic mice," 379 NATURE 632-635 (Feb. 15, 1996).

* cited by examiner

*Primary Examiner*—Lorraine Spector
*Assistant Examiner*—Shulamith H Shafer
(74) *Attorney, Agent, or Firm*—TraskBritt

(57) ABSTRACT

The present invention relates to a functional fragment of a receptor having a function in signaling. Particularly, the present invention relates to a functional fragment of the leptin receptor, involved in SOCS3, CIS and/or Vav signaling.

2 Claims, 4 Drawing Sheets

A

B

SEQUENCE LISTING

```
<160> NUMBER OF SEQ ID NOS: 30

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: functional
                        fragment of the leptin receptor

<400> SEQUENCE: 1
```

```
Tyr Leu Gly Val Thr Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: functional
                        fragment of the leptin receptor

<400> SEQUENCE: 2

Tyr Leu Gly Ile Thr Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: functional
                        fragment of the leptin receptor

<400> SEQUENCE: 3

Phe Leu Gly Val Thr Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: functional
                        fragment of the leptin receptor

<400> SEQUENCE: 4

Phe Leu Gly Ile Thr Ser
1               5

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: functional
                        fragment of the leptin receptor
<220> FEATURE:
<221> NAME/KEY: MISC_FEATURE
<222> LOCATION: (2)..(4)
<223> OTHER INFORMATION: Xaa from position 2 to 4 may be any amino acid
<220> FEATURE:
<221> NAME/KEY: MISC_FEATURE
<222> LOCATION: (7)..(7)
<223> OTHER INFORMATION: Xaa from position 7 may be a Val, Ile or Leu
<220> FEATURE:
<221> NAME/KEY: MISC_FEATURE
<222> LOCATION: (8)..(8)
<223> OTHER INFORMATION: Xaa from position 8 may be a Cys or Tyr
<220> FEATURE:
<221> NAME/KEY: MISC_FEATURE
<222> LOCATION: (12)..(12)
<223> OTHER INFORMATION: Xaa from position 12 may be a Val or Ile
<220> FEATURE:
<221> NAME/KEY: MISC_FEATURE
<222> LOCATION: (15)..(15)
<223> OTHER INFORMATION: Xaa from position 15 may be a Val or Ile
<220> FEATURE:
<221> NAME/KEY: MISC_FEATURE
<222> LOCATION: (16)..(17)
<223> OTHER INFORMATION: Xaa from position 16 to 17 may be any amino
                        acid
```

```
<400> SEQUENCE: 5

Asn Xaa Xaa Xaa Lys Ser Xaa Xaa Phe Leu Gly Xaa Thr Ser Xaa Xaa
1               5                   10                  15

Xaa Arg Glu Ser
        20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: functional
                        fragment of the leptin receptor
<220> FEATURE:
<221> NAME/KEY: MISC_FEATURE
<222> LOCATION: (2)..(4)
<223> OTHER INFORMATION: Xaa from position 2 to 4 may be any amino acid
<220> FEATURE:
<221> NAME/KEY: MISC_FEATURE
<222> LOCATION: (7)..(7)
<223> OTHER INFORMATION: Xaa from position 7 may be a Val or Ile
<220> FEATURE:
<221> NAME/KEY: MISC_FEATURE
<222> LOCATION: (8)..(8)
<223> OTHER INFORMATION: Xaa from position 8 may be a Cys or Tyr
<220> FEATURE:
<221> NAME/KEY: MISC_FEATURE
<222> LOCATION: (12)..(12)
<223> OTHER INFORMATION: Xaa from position 12 may be a Val or Ile
<220> FEATURE:
<221> NAME/KEY: MISC_FEATURE
<222> LOCATION: (15)..(15)
<223> OTHER INFORMATION: Xaa from position 15 may be a Val or Ile
<220> FEATURE:
<221> NAME/KEY: MISC_FEATURE
<222> LOCATION: (16)..(17)
<223> OTHER INFORMATION: Xaa from position 16 to 17 may be any amino
                        acid

<400> SEQUENCE: 6

Asn Xaa Xaa Xaa Lys Ser Xaa Xaa Tyr Leu Gly Xaa Thr Ser Xaa Xaa
1               5                   10                  15

Xaa Arg Glu Ser
        20

<210> SEQ ID NO 7
<211> LENGTH: 16
<212> TYPE: PRT
<213> ORGANISM: Artificial Sequence
<220> FEATURE:
<223> OTHER INFORMATION: Synthesized peptide, Sequence starts with
                        biotin-Q
<220> FEATURE:
<221> NAME/KEY: MISC_FEATURE
<223> OTHER INFORMATION: Tyr985 is phosphorylated

<400> SEQUENCE: 7

Gln Arg Gln Pro Ser Val Lys Tyr Ala Thr Leu Val Ser Asn Asp Lys
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Synthesized peptide, Sequence starts with
                        biotin-N
<220> FEATURE:
<221> NAME/KEY: MISC_FEATURE
<223> OTHER INFORMATION: Tyr1077 is phosphorylated
```

```
<400> SEQUENCE: 8

Asn His Arg Glu Lys Ser Val Cys Tyr Leu Gly Val Thr Ser Val Asn
1               5                   10                  15

Arg

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: forward
                        primer for amplification of Rat SOCS3 cDNA

<400> SEQUENCE: 9
gaagatctgt gcgccatggt cacccacagc aagtt                              35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: reverse
                        primer for amplification of Rat SOCS3 cDNA

<400> SEQUENCE: 10
gctctagatt ttgctcctta aagtggagca tcata                              35

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: forward
                        primer for reamplification of the SOCS3
                        fragment

<400> SEQUENCE: 11
gcgagatctc agaattcgtc acccacagca agtttcc                            37

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: N-terminal
                        FLAG-tag sequence

<400> SEQUENCE: 12

Met Asp Tyr Lys Asp Asp Asp Asp Lys
1               5

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: primer used
                        for amplification of the 158 AA C-terminal part
                        of human gp130

<400> SEQUENCE: 13
gacgggcccg ccaccatgga ttacaaggat gacgacgata agatctcgac cgtggtacac    60
agtggc                                                              66

<210> SEQ ID NO 14
```

```
<211> LENGTH: 35
<212> TYPE: DNA
<213> ORGANISM: Artificial Sequence
<220> FEATURE:
<223> OTHER INFORMATION: Description of Artificial Sequence: primer used
                        for amplification of the 158 AA C-terminal part
                        of human gp130

<400> SEQUENCE: 14
gcgaattccg aaccgccctg aggcatgtag ccgcc                                 35

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: primer for
                        amplification of a fragment of the SV40-T
                        antigen

<400> SEQUENCE: 15
gcgaattcga agcagaggaa actaaacaag tg                                    32

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: primer for
                        amplification of a fragment of the SV40-T
                        antigen

<400> SEQUENCE: 16
cgtctagagc ggccgcagat ctcgagtcgc gattatgttt caggttcagg gggag           55

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: forward
                        primer for murine CIS amplification

<400> SEQUENCE: 17
gcggaattcg tcctctgcgt acagggatc                                        29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: reverse
                        primer for murine CIS amplicication

<400> SEQUENCE: 18
gcctctagat cagagttgga agggtactg                                        30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:
                        primer MBU-O-737

<400> SEQUENCE: 19
gcggaattca agctggagga atgttctca                                        29
```

```
<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: primer
      MBU-O-738

<400> SEQUENCE: 20
gcctcgagtt acacgtagtt ggcagggaac c                               31

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: primer
      MBU-O-993

<400> SEQUENCE: 21
tcctgtgcac attcccatga ccatggctgt tcagtgacat ca                   42

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: primer
      MBU-O-994

<400> SEQUENCE: 22
tgatgtcact gaacagccat ggtcatggga atgtgcacag ga                   42

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: primer
      MBU-O-885

<400> SEQUENCE: 23
gatttcacca caactttgat atccggggtt ggatgagc                        38

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: primer
      MBU-O-886

<400> SEQUENCE: 24
gctcatccaa ccccggatat caaagttgtg gtgaaatc                        38

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: primer
      MBU-O-887

<400> SEQUENCE: 25
gaaagcagtt ctatttgata tcgtgaccag tgtaacag                        38
```

```
<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: primer
                        MBU-O-888

<400> SEQUENCE: 26
ctgttacact ggtcacgata tcaaatagaa ctgctttc                              38

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: primer
                        MBU-O-924

<400> SEQUENCE: 27
cacctccgtc aacagagcgg ctagcggtgt gcttttgact ggtg                       44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: primer
                        MBU-O-925

<400> SEQUENCE: 28
caccagtcaa aagcacaccg ctagccgctc tgttgacgga ggtg                       44

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: primer
                        MBU-O-1045

<400> SEQUENCE: 29
gcagaattca ccctgcggtg cctggagcc                                       29

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: primer
                        MBU-O-1046

<400> SEQUENCE: 30
gctgcggccg cttatacctg gaatttatat tcttcc                               36
```

US 7,235,629 B2

FUNCTIONAL FRAGMENT OF THE LEPTIN RECEPTOR

CROSS-REFERENCE TO RELATED APPLICATIONS

This application is a national stage entry of PCT/EP01/12569, filed Oct. 29, 2001, designating the United States of America, corresponding to PCT International Publication WO 02/40543 (published in English on May 23, 2002), which claims the benefit of EP Application 00204001.2, filed Nov. 14, 2000, and which also claims the benefit under 35 U.S.C. § 119(e) of U.S. Provisional Application 60/248,970 filed Nov. 15, 2000.

TECHNICAL FIELD

The present invention relates to a functional fragment of a receptor important in signaling. Particularly, the present invention relates to a functional fragment of the leptin receptor, involved in SOCS3, CIS and/or Vav signaling.

BACKGROUND

Leptin, an adipocyte-derived hormone, delivers its appetite-suppressing signals by passing the blood-brain barrier and binding to the specific signaling form of its receptor in certain nuclei of the hypothalamus. In this way, leptin constitutes a feedback mechanism regulating adipose tissue mass. Mutations within the leptin system result in a marked obese phenotype and impaired endocrinological functioning. (Zhang et al., 1994; Chen et al., 1996.) Although the long signaling form of the leptin receptor shows high expression levels in these hypothalamic nuclei, it is also expressed in several peripheral tissues including lung, liver, lymph nodes and gonads. (Tartaglia et al., 1995; Ghilardi et al., 1996.) This leads to the involvement of leptin in several peripheral functions and makes a typical pleiotropic cytokine.

Until today, the therapeutic use of leptin as a weight-reducing agent was limited. (Heymsfield et al., 1999.) It is observed that in most obese people, a strong correlation exists between adipose mass and leptin levels, a phenomenon often explained by leptin resistance. (Maffei et al., 1995.) A number of possible explanations for this resistance have been suggested and include: a saturable transport through the blood-brain barrier resulting in a limited leptin activity in the hypothalamus (Schwartz et al., 1996; E l Haschimi et al., 2000), cross-talk with the glucocorticoid system (Zakrzewska et al., 1997), or defects at the leptin receptor level, such as elevated expression of the signaling inhibitor SOCS3 (Bjorbaek et al., 1998).

Recently, it became clear that leptin not only plays a role in regulating food intake, but also functions in angiogenesis. (Sierra-Honigmann et al., 1998.) Further, leptin functioning in invasiveness of kidney and colonic epithelial cells (Attoub et al., 2000) have been demonstrated.

Being a member of the type 1 cytokine receptor family, the leptin receptor is activated by cross-phosphorylation of associated JAK kinases, most likely JAK2 and/or JAK1. (Bjorbaek et al., 1997; Banks et al., 2000.) Activation of the leptin receptor leads to recruitment of signaling molecules containing phosphotyrosine-binding SH2 molecules. Signal Transducers and Activators of Transcription (STAT) molecules (Baumann et al., 1996; Vaisse et al., 1996) and the receptor-associated SH2-containing phosphatase SHP-2 (Carpenter et al., 1998; Li and Friedman, 1999) are recruited in the activated leptin receptor complex. Leptin-mediated activation of Mitogen-Activated Protein Kinases (MAPK) and Insulin Receptor Substrate 1 (IRS-1) have been shown in various cell systems. (Cohen et al., 1996; Bjorbaek et al., 1997; Takahashi et al., 1997; Banks et al., 2000.) Promotion of invasiveness by leptin seems to be mediated by phosphoinositide 3-kinase, Rho- and Rac-dependent signaling pathways. (Attoub et al., 2000.)

Leptin rapidly induces Cytokine-Inducible SH2-containing protein (CIS), both in vitro and in vivo. Leptin can also strongly and rapidly induce the production of the signal transduction inhibitor Suppressor of Cytokine Signaling 3 (SOCS3) in various cell types and in vivo. (Bjorbaek et al., 1998; Emilsson et al., 1999; Waelput et al., 2000.) Both CIS and SOCS3 are members of an expanding family of SH2 containing proteins which are typically built up of a pre-SH2 domain, a central SH2 domain and a highly conserved SOCS box sequence. The latter motif is also found in a number of other signaling molecules (Hilton et al., 1998) and seems to be connected with proteasome function. (Zhang et al., 1999.) The observation that the leptin-resistant $A^y/a$ mutant mice strain shows elevated SOCS3 levels makes this protein a possible mediator of leptin resistance. (Bjorbaek et al., 1998.)

Recently, it has been shown that a tyrosine recruitment site within gp130, the signaling component of the IL-6 complex, is required for binding and, thus, for the inhibitory activity of SOCS3. (Nicholson et al., 2000; Schmidt et al., 2000.) This is in contrast to SOCS1, which binds directly to JAK kinases and directly inhibits their kinase activity. (Yasukawa et al., 1999.) Similar results have been obtained for the insulin receptor and the erythropoietin receptor. (Emanuelli et al., 2000; Sasaki et al., 2000.)

In previous studies, it has been shown that leptin induces two gene sets in the PC12 rat pheochromocytoma cell line stably expressing the mouse leptin receptor. Many of these genes appear to be regulated in vivo. (Waelput et al., 2000.) Using a mutational approach, it was shown that in the mouse leptin receptor residue Y985 is involved in a negative feedback signal, and furthermore, that this effect is more pronounced when mutated in concert with another tyrosine, Y1077. (Eyckerman et al., 1999.) However, phosphorylation of this tyrosine has never been demonstrated, suggesting that this site was playing only a minor role. Surprisingly, a short functional fragment around the Y1077 was found to be sufficient for SOCS3 and CIS binding and/or signaling. Moreover, it was demonstrated that the functional fragment is also sufficient for Vav signaling. Vav seems to be a general signaling molecule, but has never been shown to be involved in leptin signaling. The short functional sequence is extremely conserved, which makes it an attractive target for pharmaceutical compositions modulating SOCS3, CIS and/or Vav-mediated signaling in general, and leptin-induced signaling in particular.

SUMMARY OF THE INVENTION

In one embodiment of the invention, a functional fragment of a receptor comprising a sequence selected from the group of sequences consisting of SEQ ID NO: 1, SEQ ID NO:2, SEQ ID NO:3 and SEQ ID NO:4 is disclosed. The functional fragment may essentially consist of a sequence selected from the group of sequences consisting of SEQ ID NO:1, SEQ ID NO:2, SEQ ID NO:3 and SEQ ID NO:4 wherein the sequence of the functional fragment is embedded in an entire sequence of about 50 amino acids, in a sequence of about 30 amino acids or in a sequence of about 20 amino acids. The functional fragment may also comprise the sequences of SEQ ID NO:5 or SEQ ID NO:6.

When the functional fragment of the present invention is involved in SOCS3, CIS and/or Vav signaling, the functional fragment is SEQ ID NO:1, SEQ ID NO:2 or SEQ ID NO:6. When the functional fragment is involved in Vav signaling, the functional fragment is SEQ ID NO:3, SEQ ID NO:4 or SEQ ID NO:5. In cases where the sequence includes a tyrosine residue, the tyrosine residue may or may not be phosphorylated. In cases where the functional fragment is involved in SOCS3 and CIS signaling, the tyrosine residue is phosphorylated. The phosphorylation may be carried out by an associated kinase, e.g., a JAK kinase, such as JAK2 that binds on another domain of the receptor, or by a kinase activity inherent to the receptor itself.

Indeed, although the functional fragment is derived from the cytoplasmic domain of the leptin receptor, it should be evident by the person of ordinary skill in the art that it can be incorporated in other receptors such as, as a nonlimiting example, the cytokine receptor family or the protein tyrosine kinase family where the functional fragment can function as a recruitment site for signaling molecules.

In a further embodiment of the invention, the functional fragment is used to modulate ligand-induced signaling. For instance, the functional fragment may be involved in SOCS3 signaling, which is known to be a suppressor of cytokine signaling. Incorporation of the functional fragment in a cytokine receptor is, therefore, expected to modulate the cytokine-induced signaling. A similar effect is expected in other receptors due to the involvement of Vav signaling. In one embodiment, the functional fragment is used to modulate leptin-induced signaling. Such modulation may not only be useful in food intake disorders and regulation of body weight, but also in other leptin-mediated phenomena such as angiogenesis, wound healing and susceptibility to digestive cancers. The modulation of the latter may be important as Vav has been shown to bind to the functional fragment and Vav is known to act as a guanosine nucleotide exchange factor for Rac-1, which is involved in leptin-induced invasiveness of kidney and colonic epithelial cells. (Attoub et al., 2000.)

In another embodiment of the invention, the functional fragment is used to screen compounds that interfere with the binding of the functional fragment with a signaling molecule. Indeed, a receptor can be constructed, wherein the functional fragment is the only functional fragment, such as, as a nonlimiting example, a mouse leptin receptor in which the tyrosine residues at positions 985 and 1138 have been replaced by a phenylalanine. This receptor including the functional fragment may be expressed in a suitable host cell. Binding of a ligand on the receptor may induce a reporter gene, wherein the induction is mediated by binding of a signaling molecule to the functional fragment. By bringing the host cell in contact with a library of small molecules or by transfecting the host cell with a library encoding potentially inhibiting peptides, compounds inhibiting the binding of a signaling molecule with the functional fragment can be identified by selecting the host cells that do not show an induction of the reporter gene upon contacting the receptor with its ligand. Alternatively, the induction of the signaling pathway may be monitored, instead of the induction of a reporter gene.

In yet another embodiment, a compound isolated by screening with the functional fragment of the present invention is disclosed. The compound can be, as a nonlimiting example, a soluble peptide having the same sequence as the functional fragment, or a peptido-mimetic thereof, an antibody, binding to the functional fragment, or an antibody binding to a domain in SOCS3, CIS or Vav that binds directly or indirectly to the functional fragment.

BRIEF DESCRIPTION OF THE DRAWINGS

FIG. 3 depicts Western blot analysis of SOCS3 expression. The FLAG-tagged SOCS3 protein was revealed in lysates of transfected cells using anti-FLAG antibody. LRlo: leptin receptor long isoform.

pMET7-mLR F3 Del2+pMG1-VavS+pXP2d2-rPAP11uci+pUT651; and pMET7-mLR F3 Del3+pMG1-VavS+pXP2d2-rPAP11uci+pUT651.

The results are presented as fold induction compared to the nonstimulated negative control. (L: stimulation with leptin; NC: nonstimulated negative control).

Figure 7:
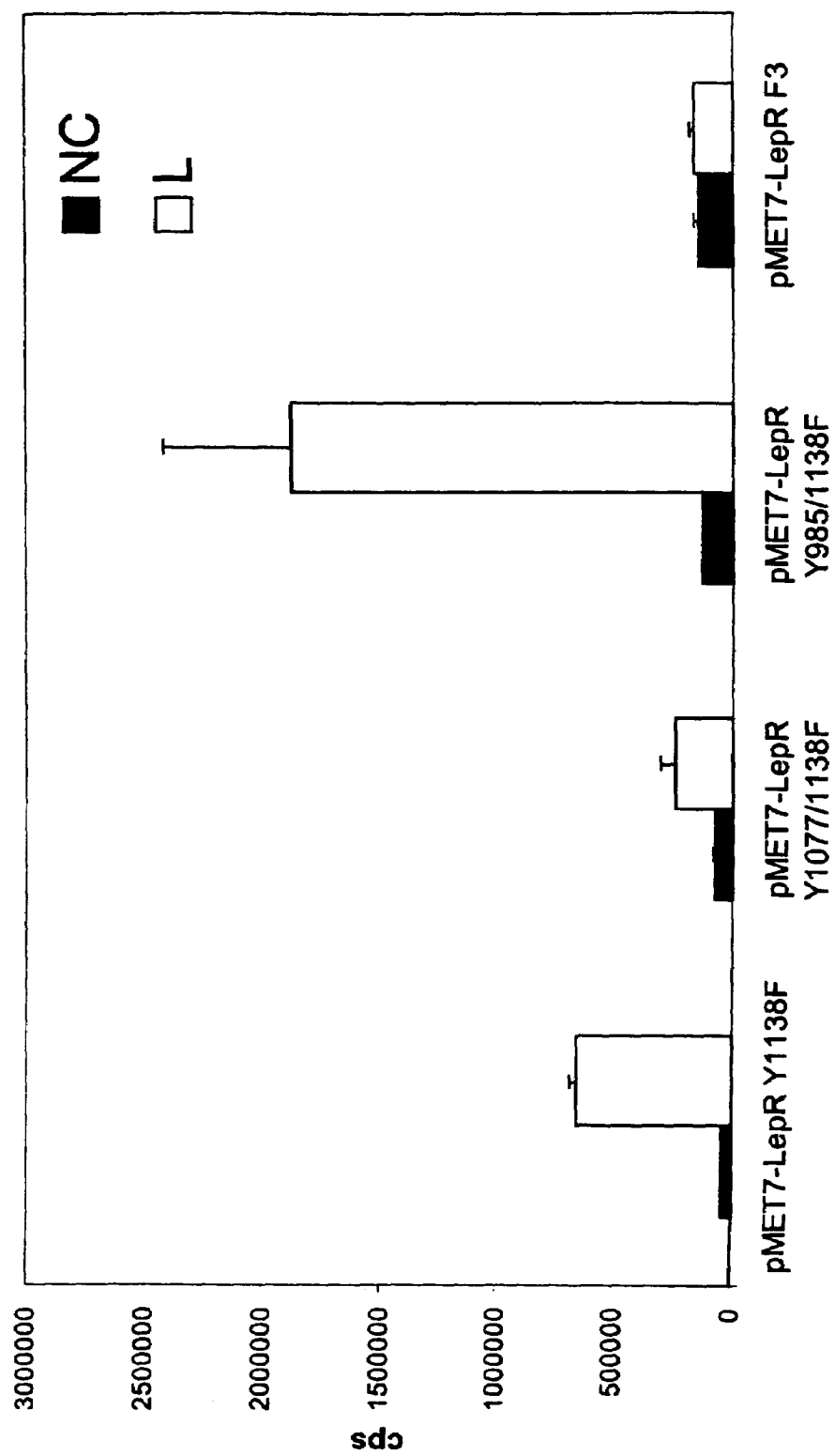

FIG. 7: CIS2 binds to both the Y985 and Y1077 motifs in the leptin receptor. HEK293T cells were transiently co-transfected with the pXP2-rPAP11uci, pMG1-CIS2 and pMET7-LR mutants as indicated. Thirty-six hours post-transfection, cells were stimulated with leptin for 24 hours (open bars) or were left untreated (solid bars). Luciferase activity is indicated as the mean of triplicate measurements +/− SD/ β-galactosidase activity from pUT561 was used to normalize for variations in transfection efficiencies. CPS: light counts per second. (L: stimulation with leptin; NC: nonstimulated negative control).

DETAILED DESCRIPTION

Definitions.

"Functional fragment" as used herein is a peptide or polypeptide, optionally carrying one or more modifications, which, when integrated in a suitable receptor molecule, functions as a binding site for one or more signaling molecules. This binding may be either constitutive or ligand induced.

"Modification" as used herein may be any modification of an amino acid known by the person of ordinary skill in the art, such as, as a nonlimiting example, phosphorylation, glycosylation or ubiquitinilation.

"Essentially consisting" as used herein means that the cited SEQ ID NO: is embedded in a total functional fragment of only 50 amino acids, preferably only 30 amino acids, even more preferably about 20 amino acids.

"Compound" as used herein means any chemical or biological compound, including simple or complex organic or inorganic molecules, peptides, peptido-mimetics, proteins, antibodies, carbohydrates, nucleic acids or derivatives thereof.

"Bind(ing)" as used herein means any interaction, be it direct or indirect. A direct interaction implies a contact between the binding partners. An indirect interaction means any interaction wherein the interaction partners interact in a complex of more than two compounds. The interaction can be completely indirect, with the help of one or more bridging molecules, or partly indirect, where there is still a direct contact between the partners, which is stabilized by the additional interaction of one or more compounds.

"Signaling molecule" as used herein means any molecule that is involved in the transfer or the inhibition of the transfer of an activated receptor to a reporter gene. In that respect, a molecule that is not directly involved in signaling itself, but that, by binding on the receptor can inhibit another molecule from binding and inducing the signaling pathway is also considered as a signaling molecule.

"Reporter gene" is any gene that leads to a detectable signal and can be, as a nonlimiting example, an antibiotic resistance gene, a toxin gene resulting in cell death, a gene encoding a fluorescent protein such as GFP, or a gene encoding an enzyme activity such as β-galactosidase. The coding sequence is placed under control of a suitable promoter, i.e., a promoter that is induced by binding of a ligand to the receptor and consequent induction of the reporter pathway.

EXAMPLES

Materials and Methods to the Examples

Antibodies, Growth Factors and Peptides.

Monoclonal anti-FLAG antibody M2 was obtained from Sigma. Mouse recombinant leptin was purchased from R&D Systems. Peptides were synthesized using standard Fmoc-amino-acid solid phase chemistry on an Applied Biosystems Model 431A peptide synthesizer. Biotin was manually esterified following similar procedures as on the synthesizer and added to the reaction mixture. Incorporation of phosphotyrosine was realized by using a protected Fmoc-tyrosine-phosphobenzylester (Novabiochem). After purification, the mass of the peptides was confirmed by mass spectrometry. Sequences of the peptides were biotin-QRQPSVK(p)Y$_{985}$ATLVSNDK (SEQ ID NO:7) and biotin-NHREKSVC(p)Y$_{1077}$ LGVTSVNR (SEQ ID NO:8).

Vectors

Generation of the Leptin Receptor Mutants, the LepR F3 Deletion and mLR F3 Point Mutants.

Generation of the leptin receptor mutants was described by Eyckerman et al. (1999). The mutant leptin receptor (long isoform) is indicated as mLR. MLR F3 is the mutant where all the cytoplasmic residues are mutated to phenylalanine.

Through site-directed mutagenesis (Quikchange™, Stratagene), three deletion and one point mutant of the mLR F3, cloned in the pMET7 expression vector, were constructed. The deletion mutants LR F3 Del1 (aa: 1-1103), LR F3 Del2 (aa: 1-1050) and LR F3 Del3 (aa: 1-952) were created by mutating Ala on position 1104 (primer combinations MBU-O-993 and MBU-O-994), Ser on position 1051 (primer combination MBU-O-885 and MBU-O-886), and Cys on position 953 (primer combination MBU-O-887 and MBU-O-888), to a STOP-codon, respectively. In each case, an extra EcoRV restriction site was simultaneously built in to distinguish mutated from parental DNA.

Construction of pMET7fSOCS3.

Rat SOCS3 cDNA was amplified using 5'-GAAGATCT-GTGCGCCATGGTC ACCCACAGCAAGTT (SEQ ID NO:9) and 5'-GCTCTAGATTTTGCTCCTTAAAGTG GAGCATCATA (SEQ ID NO: 10) as forward and reverse primers, respectively, and using mRNA from leptin-stimulated PC12 cells as template. cDNA was prepared using a standard RT procedure with Superscript Reverse Transcriptase (LifeTechnologies). Amplification was realized using Pfu polymerase (Stratagene). The SOCS3 fragment was re-amplified using forward primer 5'-GCGAGATCT-CAGAATTCGTCACCCACAGCAAGTTTCC (SEQ ID NO:11) and the reverse primer described above, which allows BglII-XbaI-based cloning in a pMET7 variant containing an N-terminal FLAG tag sequence (MDYKD-DDDK) (SEQ ID NO:12), resulting in pMET7fSOCS3.

Construction of pMG1-CIS.

CIS constructs were generated in the pMET7 vector under control of the SRα promoter. Using site-directed mutagenesis (Quikchange™, Stratagene), a unique ApaI restriction site was generated between the SRα promoter and the EcoRI site in the pMET7mcs construct, a pMET7-derivative containing a multiple cloning site. The 158 amino acid C-terminal part of human gp130 was amplified using primers 5'-GACGGGCCCGCCACCATGGATTACAA GGATGAC-GACGATAAGATCTCGACCGTGGTACACAGTGGC (SEQ ID NO:13) and 5'-GCGAATTCCGAACCGCCCT-GAGGCATGTAGCCGCC (SEQ ID NO:14). The forward primer also encodes the FLAG-tag sequence (MDYKD-DDDK) (SEQ ID NO:12) and contains ApaI and BglII sites. The reverse primer contains a GGS hinge sequence and an EcoRI restriction site allowing ApaI-EcoRi-based cloning in the pMET7 construct, resulting in the pMG1 basic vector.

A fragment of the SV40-T antigen (amino acid 261-708) was amplified using primers 5'-GCGAATTCGAAGCA-GAGGAAACTAAACAAGTG (SEQ ID NO:15) and 5'-CGTCTAGAGCGGCCGCAGATCTC-GAGTCGCGATTATGTTTCAGGTTCAGGGGGAG (SEQ ID NO:16). The N-terminal part of SV40-T containing the nuclear localization signal was deleted to prevent nuclear shuttling. The forward primer contains an EcoRI site and the reverse primer contains a stop codon and NruI, XhoI, BglIH, NotI and XbaI restriction sites. Ligating this fragment in the pMG1 vector results in the pMG1-SVT vector.

Murine CIS was amplified with forward primer 5'-GCG-GAATTCGTCCTCTGCG TACAGGGATC (SEQ ID NO:17) and with reverse primer 5'-GCCTCTAGATCA-GAGTTGGAA GGGGTACTG (SEQ ID NO:18). EcoRI-XbaI based cloning in the pMG1-SVT construct resulted in the pMG1-CIS plasmid.

TF1 cell line by standard RT-PCR techniques. Primers were MBU-O-737 and MBU-O-738 as forward and reverse primers, respectively. MBU-O-737 contains an extra EcoRI allowing in-frame fusion to gp130, and MBU-O-738 contains a stop codon and a XhoI recognition site. The amplified fragment was subcloned in de pCR®-Blunt vector and ligated in the pMG1 vector through an EcoRi-XhoI-based exchange, resulting in pMG1-VavS.

Construction of the Reporter Plasmids.

The pUT651 construct expressing β-galactosidase was obtained from Eurogentec. Generation of the pGL3-rPAP1-luci construct was described by Eyckerman et al. (1999). The full-length rPAP1 promoter fragment was excised using partial digestion with KpnI and XhoI and ligated into the KpnI-XhoI-digested pXP2d2 vector (gift from Prof. S. Nordeen), resulting in the leptin-responsive pXP2d2-rPAP1-luci reporter construct. The pXP2d2 vector is a derivative of pXP2 that lacks potential cryptic Activator Protein 1 sites (Grimm and Nordeen, 1999).

All constructs were verified by restriction and sequence analysis.

Oligonucleotide table.

| | | | |
|---|---|---|---|
| MBU-O-737 | hVavS primer F | 5'-GCGGAATTCAAGCTGGAGGAATGTTCTCA | (SEQ ID NO:19) |
| MBU-O-738 | hVavS primer R | 5'-GCCTCGAGTTACACGTAGTTGGCAGGGAACC | (SEQ ID NO:20) |
| MBU-O-993 | mLR F3 Del1 mutagenesis F | 5'-TCCTGTGCACATTCCCATGACCATGGCTGTTCAGTGACATCA | (SEQ ID NO:21) |
| MBU-O-994 | mLR F3 Del1 mutagenesis R | 5'-TGATGTCACTGAACAGCCATGGTCATGGGAATGTGCACAGGA | (SEQ ID NO:22) |
| MBU-O-885 | mLR F3 Del2 mutagenesis F | 5'-GATTTCACCACAACTTTGATATCCGGGGTTGGATGAGC | (SEQ ID NO:23) |
| MBU-O-886 | mLR F3 Del2 mutagenesis R | 5'-GCTCATCCAACCCCGGATATCAAAGTTGTGGTGAAATC | (SEQ ID NO:24) |
| MBU-O-887 | mLR F3 Del3 mutagenesis F | 5'-GAAAGCAGTTCTATTTGATATCGTGACCAGTGTAACAG | (SEQ ID NO:25) |
| MBU-O-888 | mLR F3 Del3 mutagenesis R | 5'-CTGTTACACTGGTCACGATATCAAATAGAACTGCTTTC | (SEQ ID NO:26) |
| MBU-O-924 | mLR Fall R225A/E226A mutagenesis F | 5'-CACCTCCGTCAACAGAGCGGCTAGCGGTGTG CTTTTGA CTGGTG | (SEQ ID NO:27) |
| MBU-O-925 | mLR Fall R225A/E226A mutagenesis R | 5'-CACCAGTCAAAAGCACACCGCTAGCCGCTCTGTTGACG GAGGTG | (SEQ ID NO:28) |
| MBU-O-1045 | CIS2 primer F | 5'-GCAGAATTCACCCTGCGGTGCCTGGAGCC | (SEQ ID NO:29) |
| MBU-O-1046 | CIS2 primer R | 5'-GCTGCGGCCGCTTATACCTGGAATTTATATTCTTCC | (SEQ ID NO:30) |

Construction of pMG1-CIS2.

A fragment of human CIS2 (aa 34-198) containing the SH2 domain and the SOCS box sequence was amplified via RT-PCR using primers MBU-O-1046 and MBU-O-1047 as forward and reverse primers, respectively. The forward primer contains an EcoRI site while the reverse primer contains the stop codon and a NotI restriction site. RNA from HEK293 c116 cells was used as input in a one-step RT-PCR procedure (Qiagen Onestep RT-PCR kit). EcoRi-NotI-based cloning in pMG1-SVT resulted in pMG1-CIS2.

Construction of pMG1-VavS.

A fragment of human Vav1 (VavS: aa 259-789) was amplified using Pfu polymerase from mRNA of the human Cell Lines and Transfection Procedures.

Culture conditions and transient transfection procedures for PC12 and generation of the PC12LR8 cell line were as previously described. (Eyckerman et al., 1999; Waelput et al., 2000.)

HEK293T cells were maintained in a 10% $CO_2$ humidified atmosphere at 37° C. and grown using DMEM with 4500 mg/l glucose, 10% fetal bovine serum and 50 μg/ml gentamycin (all from LifeTechnologies). Typically, $4 \times 10^5$ cells were seeded the day before transfection in a 6-well plate and transfected overnight with approximately 2 μg plasmid DNA using a standard calcium phosphate precipitation procedure. One day after transfection, cells were re-suspended with Cell Dissociation Agent (LifeTechnologies), seeded in a black well plate (Costar) and stimulated overnight with 100 mg/ml leptin or left unstimulated.

Reporter Assays and Northern Blot.

Luciferase assays, binding assays using Leptin-SEAP and Northern blot hybridizations with SOCS3 and actin probes were described previously by Eyckerman et al. (1999). β-galactosidase activity was measured using the Galacto-Star™ chemiluminescent detection kit (Tropix) and a Topcount Chemiluminescence Counter (Packard).

Western Blot Analysis and Phosphopeptide Affinity Chromatography.

Approximately $10^6$ HEK293T cells were lysed in 150 µl 2× loading buffer. After sonication, 30 µl was loaded on a 10% polyacrylamide gel. After overnight blotting, FLAG-tagged SOCS3 was revealed using a ½500 dilution of anti-FLAG antibody. Blotting efficiency was checked using PonceauS staining (Sigma).

For phosphopeptide affinity chromatography, approximately $3 \times 10^7$ HEK293T cells transiently transfected as indicated were lysed in lysis buffer (20 mM Hepes pH 7; 1 mM $MgCl_2$; 10 mM KCl; 0.5 mM DTT; 150 mM NaCl; 0.5% NP40; 1 mM $NaVO_4$; 5 mM NaF; 20% glycerol; Complete™ Protease Inhibitor Cocktail (Roche)). Precipitated material was cleared by 5 minutes centrifugation at 10,000 g. To eliminate a-specific interactions, supernatants were brought on a pre-column containing Sepharose 4B beads prior to phosphopeptide affinity chromatography on streptavidin-coupled agarose beads (Sigma). Peptide concentrations were determined by a colorimetric assay using alkaline hydrolysis and a ninhydrine reagent. Fifty µl of streptavidin-agarose slurry was incubated with 5 nmoles of peptide for each reaction. Cleared lysate was incubated for two hours at 4° C. under slow stirring. After incubation, beads were washed four times with lysis buffer and re-suspended in 2× loading buffer.

Example 1

SOCS3 Binds to the Conserved Y1077 Region

The observation that most obese human patients show elevated levels of leptin suggests the existence of a so-called leptin resistance. (Maffei et al., 1995.) SOCS3, a potential mediator of this resistance (Bjorbaek et al., 1998), is a member of a family of SH2 domain-containing proteins mostly involved in negative regulation of signal transduction pathways. (Hilton et al., 1998.)

Figure 1:
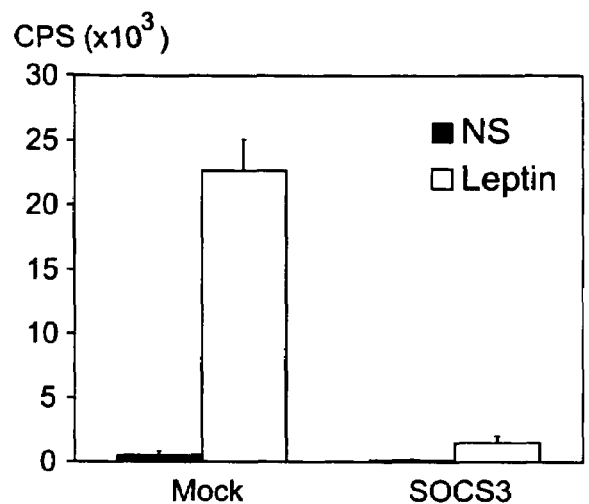
FIG. 1: Expression of SOCS3 leads to inhibition of leptin-induced rPAP1 expression in PC12 cells. PC12 LR8 cells were co-transfected with a plasmid encoding SOCS3 (pMET7fSOCS3) or empty vector (mock, pMET7), and a pGL3-rPAP11 reporter construct. Forty-eight hours after transfection, the cells were stimulated with leptin or left untreated. Luciferase activity was measured in triplicate after 24 hours. CPS: absolute luminescence counts per second; NS: nonstimulated negative control.

Through representational difference analysis, a PCR-based differential expression screening in PC12 cells expressing the mouse leptin receptor, several leptin-induced transcripts (including SOCS3) were identified. In order to check the inhibitory role of SOCS3 on leptin signaling in the cell systems used, an expression vector containing rat SOCS3 was generated. Transient expression of SOCS3 in PC12 LR8 cells, a PC12 clone that stably expresses the leptin receptor, together with the pGL3-rPAP1luci construct leads to marked inhibition of leptin-mediated reporter induction (FIG. 1). The rPAP1 promoter is derived from the rat Pancreatitis Associated Protein1 gene and shows strong induction in PC12 cells upon treatment with leptin plus forskolin. (Waelput et al., 2000.) Similar results were obtained in HEK293T cells transiently transfected with the leptin receptor, SOCS3 and the pXP2d2-rPAP1luci constructs. The pXP2d2-rPAP1luci construct showed in HEK293T cells a four times increased signal/background ratio and a higher reproducibility in comparison to the pGL3-based reporter construct. Taken together, these findings confirm the inhibitory activity of SOCS3 in our cell-based reporter systems.

The murine leptin receptor contains three tyrosine residues within its cytoplasmic domain (FIG. 2A). Y1138 is situated within a box3 or STAT3 recruitment motif and is critical for leptin-mediated gene induction. Previously, a critical role for Y985 and, to a lesser extent, also for Y1077 in the murine leptin receptor in a negative feedback signal was shown. (Eyckerman et al., 1999.) To assess the effect of Y to F mutations within the leptin receptor on SOCS3 expression itself, Northern blot analysis was performed using PC12 cells transiently transfected with leptin receptor mutants. Forty-eight hours after transfection, cells were stimulated for 24 hours with leptin (100 ng/ml) or were left untreated (FIG. 2B).

Previously obtained results indicate that SOCS3 transcription is rapidly induced in PC12 cells with an optimum around 30 minutes, but that weak SOCS3 expression persists until later time points. (Waelput et al., 2000.) Results shown in FIG. 2B imply that during this late induction phase, mutation of Y985 results in a strong up-regulation of SOCS3 transcription. This occurs only in conjunction with Y1138, a STAT3 activation site, indicating that SOCS3 expression is STAT-dependent as has been shown for signaling via the IL-6 and leukemia inhibitory factor receptors. (Auernhammer et al., 1999; Schmitz et al., 2000.) Absence of the Y1077 site does not lead to altered SOCS3 mRNA expression, but the lack of both sites results in a further increased induction level above what is observed for the Y985 mutant alone. These results are in line with the previous results for metallothionein II mRNA regulation. (Eyckerman et al., 1999.) A possible explanation for the elevated SOCS3 expression level could be the loss of negative feedback via either SOCS3 itself or, alternatively, via the SH2-containing phosphatase SHP-2. (Carpenter et al., 1998; Li and Friedman, 1999.)

Both SOCS3 and the Cytokine Inducible SH2-containing protein (CIS), another member of the SOCS family, were shown to bind activated receptors. SOCS3 binds to the gp130 signaling component of the IL-6 complex (Nicholson et al., 2000; Schmitz et al., 2000), the erythropoietin receptor (Sasaki et al., 2000) and the insulin receptor (Emanuelli et al., 2000), while CIS binds to the erythropoietin receptor, the β common chain (Yoshimura et al., 1995) and to the leptin receptor (see example 2).

Based on its functional similarity with the gp130 chain, the leptin receptor was tested for interaction with SOCS3. Leptin receptor variants containing Y to F mutations at positions Y985, Y1077, or at both sites, were tested in a functional assay based on rPAP1-induction. Signalling via the leptin receptor variants was analyzed upon transient transfection in HEK293T cells with the pXP2d2-rPAP1luci and the FLAG-tagged pMET7-fSOCS3 expression construct. Luciferase activity data were normalized by co-transfection with pUT651 and a β-galactosidase activity assay.

Figure 3:
FIG. 3: SOCS3-mediated inhibition of leptin signaling is dependent on the presence of either Y985 or Y1077 in the murine leptin receptor. Hek293T cells were transiently co-transfected with plasmids encoding different leptin receptor variants, SOCS3 or empty vector, together with the pXP2d2-rPAP11uci reporter construct.

Expression of leptin receptor variants and SOCS3 were confirmed, respectively, by a binding assay using a leptin-SEAP fusion protein and Western blot analysis using an anti-FLAG antibody (FIG. 3). LR expression levels were measured on transfected cells by incubation for 90 minutes with Leptin-SEAP fusion protein with or without excess leptin (100×). The transfected cells were stimulated for 24 hours with leptin or left untreated. Luciferase measurements were performed in triplicate and were normalized by co-transfection with the pUT651 β-galactosidase construct and a β-galactosidase activity assay. The results indicated a strong inhibitory activity of SOCS3 (80-90% inhibition) when the wild-type or the mutant Y1077F leptin receptor was expressed, and a moderate inhibition (30-50% inhibition) upon expression of a Y985F receptor variant. In the case of the double Y985/1077F mutant, no inhibition was observed.

Figure 4:
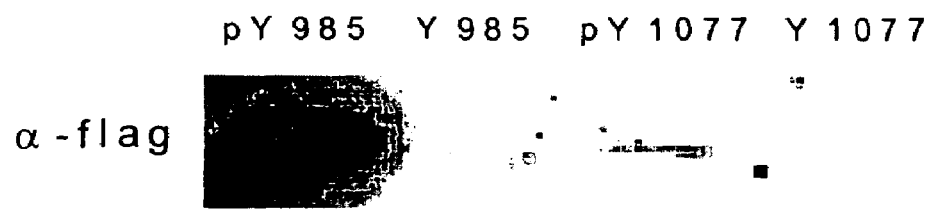
FIG. 4: SOCS3 binding to peptides matching leptin receptor Y985 and Y1077 sites is phosphorylation dependent. Lysates of Hek293T cells overexpressing FLAG-tagged SOCS3 protein were incubated with peptides matching leptin receptor Y985 and Y1077 sites, either phosphorylated or not. Specific binding of SOCS3 was revealed by immunoblotting using an anti-FLAG antibody.

The interaction sites of SOCS3 with the leptin receptor were confirmed using a biochemical approach. FLAG-tagged SOCS3 was expressed upon transient transfection of pMET7-fSOCS3 in HEK293T cells and was analyzed for binding to (phospho)-tyrosine-containing peptides matching the two motifs within the leptin receptor. Lysates of approximately $3 \times 10^7$ transfected cells were incubated with biotinylated peptides encompassing residues Y985 or Y1077 in the leptin receptor. Western blot analysis using an anti-FLAG antibody showed clear and specific binding of SOCS3 to the phosphorylated Y985 peptide, while non-phosphorylated peptide did not bind any SOCS3 protein. SOCS3 also binds specifically to the phosphorylated Y1077 peptide, but apparently with a much lower affinity confirming its accessory role in SOCS3 mediated inhibition (FIG. 4).

Figure 2:
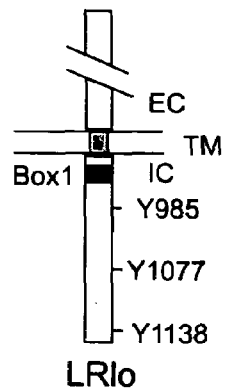
FIGS. 2A through 2B: (A) Schematic representation of the long isoform of the murine leptin receptor (LRlo), showing extracellular (EC), transmembrane (TM) and intracellular (IC) parts. The Box 1 motif and the three tyrosines involved in signal transduction are also shown. (B) Y985F and Y985/1077F, but not Y1077F mutations in the leptin receptor lead to augmented levels of SOCS3 mRNA. PC 12 cells were transiently transfected with plasmids encoding different leptin receptor variants and were stimulated with leptin for 24 hours. Northern blot analysis was performed on lysates using a rat SOCS3 probe. A β-actin probe was used for mRNA quantitation. Induction of SOCS3 is also shown for PC12 LR8 cells stably expressing the murine leptin receptor. LR: leptin receptor; sh: short isoform; lo: long isoform; F3: all cytoplasmic tyrosines mutated to phenylalanine.
Figure 2:
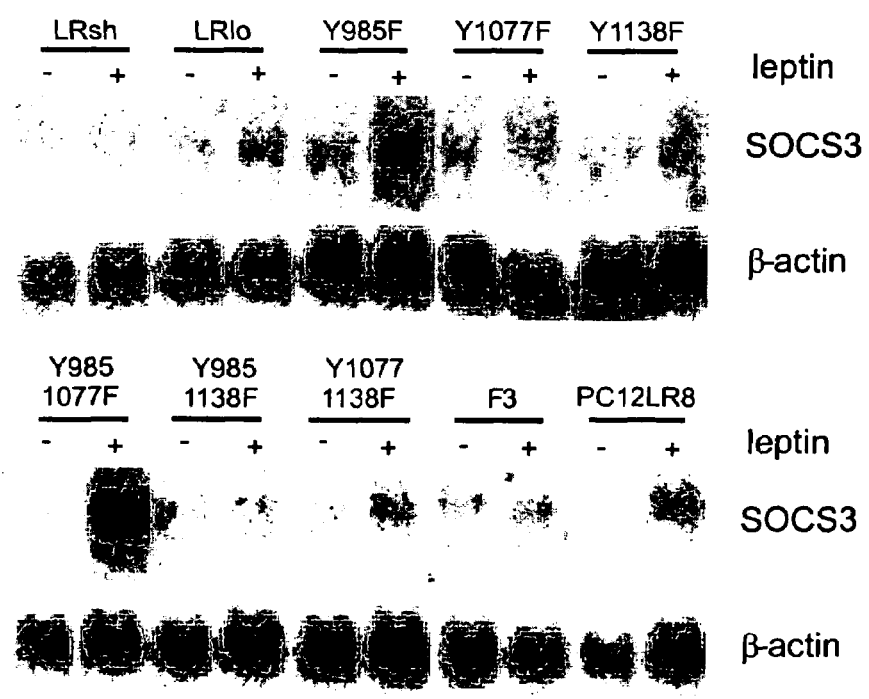

Taken together, these findings suggest that both tyrosines are involved in SOCS3 recruitment to the activated leptin receptor complex although binding to the Y1077 position apparently occurs at significantly lower efficiency suggesting an accessory role for this site. This observation could explain why, at late time points post-stimulation, the single Y1077 mutant does not lead to detectable differences on induction of metallothionein II and SOCS3 genes when compared to the wild-type receptor, whereas a more pronounced induction is observed when the double Y985/1077F mutant is compared to the Y985F receptor variant (FIG. 2).

In line with these findings, recruitment of SOCS3 at the single phosphorylated Y1077 motif shows a moderate inhibition of leptin signaling. Perhaps this accessory role of the Y1077 motif is only functional when expression levels of SOCS3 are highly elevated, suggesting different threshold levels for leptin receptor signaling may exist. Although several groups were not able to show leptin-dependent phosphorylation of the Y1077 site in the leptin receptor using anti-phosphotyrosine antibodies (Li and Friedman, 1999; Banks et al., 2000), this disclosure indicates a functional phosphorylation-dependent role for this site in leptin signaling.

It is of note that a stretch of ten amino acids downstream of the Y1077 motif is very conserved throughout evolution. This pronounced conservation of the Y1077 motif also underscores its functional importance in leptin signaling.

Example 2

CIS Binds to the Highly Conserved Y985 and Y1077 Motifs in the Leptin Receptor

Figure 5:
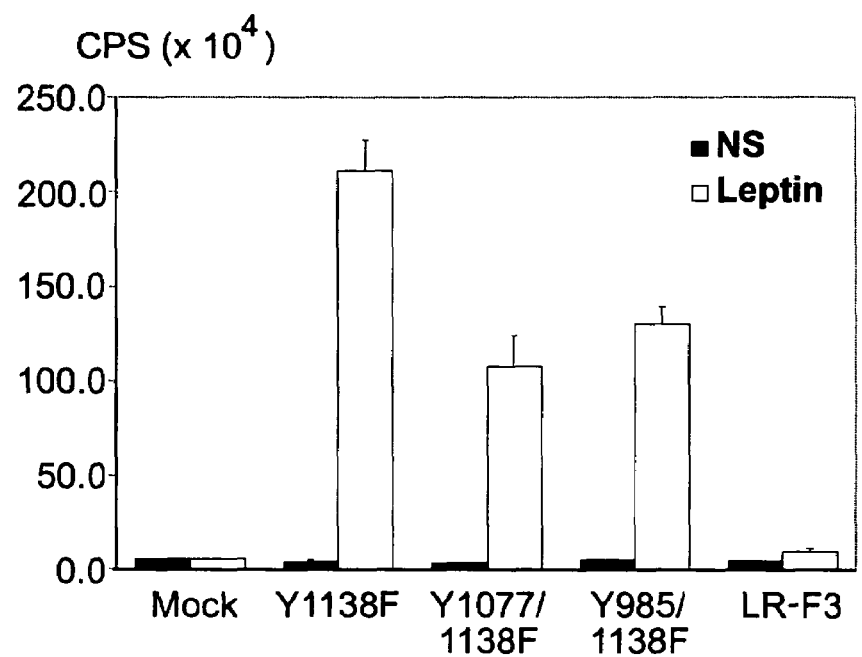
FIG. 5: CIS interacts with the Y985 and Y1077 motifs in the leptin receptor. HEK293T cells were transiently co-transfected with the pXP2d2-rPAP11uci, pMG1-CIS and pMET7-LR mutants as indicated. Thirty-six hours post-transfection, cells were stimulated with leptin for 24 hours (open bars) or were left untreated (solid bars). Luciferase activity is indicated as the mean of triplicate measurements +/− SD. β-galactosidase activity from pUT651 was used to normalize for variations in transfection efficiencies. CPS: light counts per second.

CIS expression is rapidly induced by leptin, but recruitment to the leptin receptor was never shown. Using a functional assay, binding of CIS to both phosphorylated Y985 and Y1077 motifs have been demonstrated. Leptin receptor mutants that contained the Y1138F mutation were used and resulted in lack of STAT (Baumann et al., 1996) and rPAP1 promoter (Eyckerman et al., 1999) activation. Y1138F receptor mutants containing additional Y to F substitutions at positions Y985, Y1077, or at both, were transiently co-transfected with the gp130-CIS construct and the pXP2d2-rPAP1-1uci and pUT651 reporter vectors. Normalized luciferase data are shown in FIG. 5 and indicate comparable functional recruitment of CIS to both single Y985 and Y1077 tyrosine motifs within the leptin receptor. In line with the use of both sites, a stronger signal is obtained for the single Y1138F mutant receptor. No luciferase activity is induced in case of cells transfected with pMET7-LR-F3 or with empty vector. No difference in expression levels of the mutant receptors was observed. Mutual comparison and cross-species relationship of the amino acid contexts of the Y985 and Y1077 residues support the functional data on CIS recruitment on both sites.

Example 3

Vav is Recruited by the Conserved Y1077 Region, Even without Phosphorylation of the Tyrosine Residue The functionality of the mLR F3 deletions were tested by the following transfections in Hek293T cells:

a. pMET7-mLR F3+pMG1-VavS+pXP2d2-rPAP11uci+pUT651;

b. pMET7-mLR F3 Del1+pMG1-VavS+pXP2d2-rPAP11uci+pUT651;

c. pMET7-mLR F3 Del2+pMG1-VavS+pXP2d2-rPAP11uci+pUT651; and d. pMET7-mLR F3 Del3+pMG1-VavS+pXP2d2-rPAP11uci+pUT651.

Transfection was performed as follows: A 300 µl precipitation mixture was prepared containing 3.05 µg DNA (0.05 µg of pUT651; 1 µg of each other vector). Two hundred µl of this mixture was added to $4 \times 10^5$ cells for 18 hours. After one wash with PBS-A, cells were further incubated in 3 ml DMEM medium for 24 hours. Cells were re-suspended with 200 µl cell dissociation agent and DMEM medium was added to a total volume of 2 ml. Fifty µl of this cell suspension was transferred into a 96-well plate for each transfection and stimulation with leptin (final concentration 100 ng/ml) was performed in triplicate. Twenty-four hours after stimulation, luciferase and β-galactosidase measurements were performed as described herein.

Figure 6:
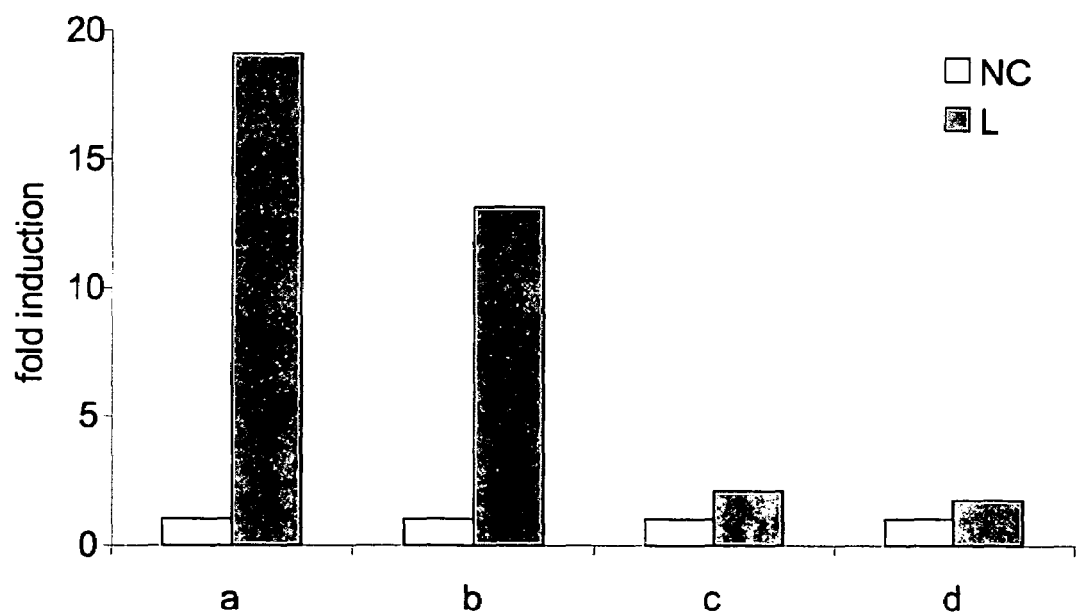
FIG. 6: Functionality of mLR F3 deletion and point mutants. Cells were transfected with:
pMET7-mLR F3+pMG1-VavS+pXP2d2-rPAP11uci+pUT651;
pMET7-mLR F3 Del1+pMG1-VavS+pXP2d2-rPAP11uci+pUT651.

As shown in FIG. 6, the results illustrate that from the three deletion mutants, only the mLR F3 Del1 (transfection b) shows a significant induction of the rPAP1 promoter. Transfections c and d, compared to the MLR F3 (transfection a), lack induction of luciferase activity with leptin.

Example 4

CIS2 Binds to Both the Y985 and Y1077 Motifs in the Leptin Receptor

A similar functional assay in HEK293T cells as in example 2 was performed. Variant leptin receptor mutants were co-transfected with the pMG1-CIS2 construct and both the pXP2d2rPAP11uci and pUT651 reporters. FIG. 7 shows normalized luciferase data. No difference in expression levels of the mutant receptors was observed. Data shown is the mean of triplicate measurements. CIS2 binds predominantly to the Y1077 site, while binding to the Y985 site is less pronounced. No significant luciferase induction is observed when the LR-F3 mutant was transfected.

REFERENCES

Attoub, S., Noe, V., Pirola, L., Bruyneel, E., Chastre, E., Mareel, M., Wymann, M. P. and Gespach, C. (2000) FASEB J. 14, 2329-2338.

Auernhammer, C. J., Bousquet, C. and Melmed, S. (1999) Proc.Natl.Acad.Sci.U.S.A. 96, 6964-6969.

Banks, A. S., Davis, S. M., Bates, S. H. and Myers, M. G., Jr. (2000) J. Biol. Chem. 275, 14563-14572.

Baumann, H., Morella, K. K., White, D. W., Dembski, M., Bailon, P. S., Kim, H., Lai, C. F. and Tartaglia, L. A. (1996) Proc.Natl.Acad.Sci.U.S.A. 93, 8374-8378.

Bjorbaek, C., Elmquist, J. K., Frantz, J. D., Shoelson, S. E. and Flier, J. S. (1998) Mol.Cell 1, 619-625.

Bjorbaek, C., Uotani, S., da Silva, B. and Flier, J. S. (1997) J. Biol. Chem. 272, 32686-32695.

Carpenter, L. R., Farruggella, T. J., Symes, A., Karow, M. L., Yancopoulos, G. D. and Stahl, N. (1998) Proc.Natl.Acad.Sci.U.S.A. 95, 6061-6066.

Chen, H., Charlat, O., Tartaglia, L. A., Woolf, E. A., Weng, X., Ellis, S. J., Lakey, N. D., Culpepper, J., Moore, K. J., Breitbart, R. E., Duyk, G. M., Tepper, R. I. and Morgenstern, J. P. (1996) Cell 84, 491-495.

Cohen, B., Novick, D. and Rubinstein, M. (1996) Science 274, 1185-1188.

E l Haschimi, K., Pierroz, D. D., Hileman, S. M., Bjorbaek, C. and Flier, J. S. (2000) J.Clin.Invest 105, 1827-1832.

Emanuelli, B., Peraldi, P., Filloux, C., Sawka-Verhelle, D., Hilton, D. and Van Obberghen, E. (2000) J.Biol.Chem. 275, 15985-15991.

Emilsson, V., Arch, J. R., de Groot, R. P., Lister, C. A. and Cawthorne, M. A. (1999) FEBS Lett. 455, 170-174.

Eyckerman, S., Waelput, W., Verhee, A., Broekaert, D., Vandekerckhove, J. and Tavernier, J. (1999) Eur.Cytokine Netw. 10, 549-556.

Ghilardi, N., Ziegler, S., Wiestner, A., Stoffel, R., Heim, M. H. and Skoda, R. C. (1996) Proc.Natl.Acad.Sci.U.S.A. 93, 6231-6235.

Grimm, S. L. and Nordeen, S. K. (1999) Biotechniques 27, 220-222.

Heymsfield, S. B., Greenberg, A. S., Fujioka, K., Dixon, R. M., Kushner, R., Hunt, T., Lubina, J. A., Patane, J., Self, B., Hunt, P. and McCamish, M. (1999) JAMA 282, 1568-1575.

Hilton, D. J., Richardson, R. T., Alexander, W. S., Viney, E. M., Willson, T. A., Sprigg, N. S., Starr, R., Nicholson, S. E., Metcalf, D. and Nicola, N. A. (1998) Proc.Natl.Acad.Sci.U.S.A. 95, 114-119.

Li, C. and Friedman, J. M. (1999) Proc.Natl.Acad.Sci.U.S.A. 96, 9677-9682.

Maffei, M., Halaas, J., Ravussin, E., Pratley, R. E., Lee, G. H., Zhang, Y., Fei, H., Kim, S., Lallone, R., Ranganathan, S. and et al. (1995) Nat.Med. 1, 1155-1161.

Nicholson, S. E., De Souza, D., Fabri, L. J., Corbin, J., Willson, T. A., Zhang, J. G., Silva, A., Asimakis, M., Farley, A., Nash, A. D., Metcalf, D., Hilton, D. J., Nicola, N. A. and Baca, M. (2000) Proc.Natl.Acad.Sci.U.S.A. 97, 6493-6498.

Sasaki, A., Yasukawa, H., Shouda, T., Kitamura, T., Dikic, I. and Yoshimura, A. (2000) J. Biol. Chem.

Schwartz, M. W., Peskind, E., Raskind, M., Boyko, E. J. and Porte, D. (1996) Nat.Med. 2, 589-593.

Sierra-Honigmann, M. R., Nath, A. K., Murakami, C., Garcia-Cardena, G. Papapetropoulos, A., Sessa W. C., Madge, L. A., Schechner, J. S., Schwabb, M. B., Polyerini, P. J. and Flores-Riveros, J. R. (1988) Science, 281, 1683-1686.

Schmitz, J., Weissenbach, M., Haan, S., Heinrich, P. C. and Schaper, F. (2000) J. Biol. Chem. 275, 12848-12856.

Takahashi, Y., Okimura, Y., Mizuno, I., Iida, K., Takahashi, T., Kaji, H., Abe, H. and Chihara, K. (1997) J. Biol. Chem. 272, 12897-12900.

Tartaglia, L. A., Dembski, M., Weng, X., Deng, N., Culpepper, J., Devos, R., Richards, G. J., Campfield, L. A., Clark, F. T. and Deeds, J. (1995) Cell 83, 1263-1271.

Vaisse, C., Halaas, J. L., Horvath, C. M., Darnell, J. E., Jr., Stoffel, M. and Friedman, J. M. (1996) Nat.Genet. 14, 95-97.

Waelput, W., Verhee, A., Broekaert, D., Eyckerman, S., Vandekerckhove, J., Beattie, J. H. and Tavernier, J. (2000) Biochem. J., 348, 55-61.

Yasukawa, H., Misawa, H., Sakamoto, H., Masuhara, M., Sasaki, A., Wakioka, T., Ohtsuka, S., Imaizumi, T., Matsuda, T., Ihle, J. N. and Yoshimura, A. (1999) EMBO J. 18, 1309-1320.

Yoshimura, A., Ohkubo, T., Kiguchi, T., Jenkins, N. A., Gilbert, D. J., Copeland, N. G., Hara, T. and Miyajima, A. (1995) EMBO J. 14, 2816-2826.

Zakrzewska, K. E., Cusin, I., Sainsbury, A., Rohner, J. F. and Jeanrenaud, B. (1997) Diabetes 46, 717-719.

Zhang, J. G., Farley, A., Nicholson, S. E., Willson, T. A., Zugaro, L. M., Simpson, R. J., Moritz, R. L., Cary, D., Richardson, R., Hausmann, G., Kile, B. J., Kent, S. B., Alexander, W. S., Metcalf, D., Hilton, D. J., Nicola, N. A. and Baca, M. (1999) Proc.Natl.Acad.Sci.U.S.A. 96, 2071-2076.

Zhang, Y., Proenca, R., Maffei, M., Barone, M., Leopold, L. and Friedman, J. M. (1994) Nature 372, 425-432.

---

The invention claimed is:

1. An isolated or recombinant peptide having no more than 50 amino acids and comprising the amino acid sequence Tyr-Leu-Gly-Val-Thr-Ser (SEQ ID NO:1) and that is able to bind to proteins Suppressor of Cytokine Signalling 3 (SOCS3), cytokine-inducible SH2-containing protein (CIS), and Vav.

2. An isolated or recombinant peptide for modulating leptin receptor mediated signaling, which peptide binds to Suppressor of Cytokine Signalling 3 (SOCS3), cytokine-inducible SH2-containing protein (CIS), and Vav, as determined by rat Pancreatitis Associated Protein 1 (rPAP1) induction, wherein said isolated or recombinant peptide comprises Tyr-Leu-Gly-Val-Thr-Ser (SEQ ID NO:1), and further wherein said isolated or recombinant peptide has no more than fifty (50) amino acids.

* * * * *